United States Patent [19]
Mack

[11] Patent Number: 5,338,193
[45] Date of Patent: Aug. 16, 1994

[54] LOCKING DEVICE FOR AN ARTICULATOR

[76] Inventor: Heinz Mack, Taxisstr. 41, D-8000 München 19, Fed. Rep. of Germany

[21] Appl. No.: 31,483

[22] Filed: Mar. 15, 1993

[30] Foreign Application Priority Data

Apr. 5, 1992 [DE] Fed. Rep. of Germany ....... 4211301

[51] Int. Cl.⁵ ............................................. A61C 11/00
[52] U.S. Cl. ........................................ 433/57; 433/66
[58] Field of Search ................... 433/54, 57, 64, 66; 403/90

[56] References Cited

U.S. PATENT DOCUMENTS

| | | | |
|---|---|---|---|
| 511,479 | 12/1893 | Westbrook | 403/90 |
| 3,048,923 | 8/1962 | Franwick | 433/57 |
| 3,478,431 | 11/1969 | DePietro | 433/57 |
| 3,624,906 | 12/1971 | Granger | 433/57 |
| 5,071,279 | 12/1991 | Rutstrom | 403/90 |

FOREIGN PATENT DOCUMENTS

| | | | |
|---|---|---|---|
| 1023077 | 12/1952 | France | 403/90 |
| 211991 | 3/1924 | United Kingdom | 403/90 |

*Primary Examiner*—Cary E. O'Connor
*Attorney, Agent, or Firm*—Larson and Taylor

[57] ABSTRACT

The invention provides a locking device for the secure hinged connection between the ball 1 and the ball housing 2 of an articulator, in the case of which on the outer side of the ball housing 2, which faces the ball neck 3, a semi-circular ledge 4 is arranged whereas on the ball neck 3 an axially movable, lockable ring 5 is provided. On the side facing the ball, the ring 5 has a circular groove 6 into which the semi-circular ledge 4 fits in a spring-loaded manner during locking.

4 Claims, 7 Drawing Sheets

LOCKING DEVICE FOR AN ARTICULATOR

FIELD OF THE INVENTION

The present invention relates to a locking device for a secure hinged connection between the ball and the ball housing of an articulator, the ball having a horizontally aligned ball neck and the ball housing being rested on the ball.

BACKGROUND OF THE INVENTION

Dental articulators have been proposed in a number of different constructions. Thus for instance the applicant's German patent specification 2,511,388 discloses a dental articulator, which essentially consists of a frame lower part with a holding device for the mounting plate for the lower jaw model and a support table for the incisor tooth guide pin, vertical frame part permanently connected with the frame lower part and having two balls functioning as joint heads and arranged on two support pins, and a frame upper part with the two radially swivel ball housings adapted to function as joint housings and which have a rear ball guiding device and an angularly adjustable inner ball fitting which is able to be adjusted in relation to the rear ball guiding device, and furthermore the bearing shaft, of the holding device for the mounting plate for the upper jaw model and an adjustable incisor tooth guiding pin.

It has turned out to be a disadvantage in the case of such articulators that the ball housings of the upper part of the articulator can not be connected with the balls of the frame upper part in such a manner that while working with the articulator it is not possible for the two parts to be accidently disconnected from each other.

SUMMARY OF THE INVENTION

Therefore one object of the present invention is to provide a locking device for an articulator, with which a secure hinged connection between the ball and the ball housing is ensured with the result that accidental detachment of the connection between the ball and the ball housing is prevented.

The invention accordingly provides a locking device for a secure hinged connection between the ball and the ball housing of an articulator, the ball having a horizontally aligned ball neck and the ball housing being rested on the ball, wherein on the outer side of the ball housing, which is turned towards the ball neck, a semi-circular ledge is provided and in that on the ball neck an axially movable and lockable ring is arranged, which on the side facing towards ball has a circular groove, into which the semi-circular ledge resiliently fits during locking. The inner diameter of the semi-circular ledge is equal to the external diameter of the ball neck.

BRIEF DESCRIPTION OF THE DRAWINGS

The present invention will furthermore be explained with reference to the FIGS. 1 through 8, which show a preferred working embodiment thereof to which the invention is not limited. All the features disclosed in the figures constitute part of the disclosure essential of the invention even although there may not be any express reference thereto in the following description.

Figure 1:
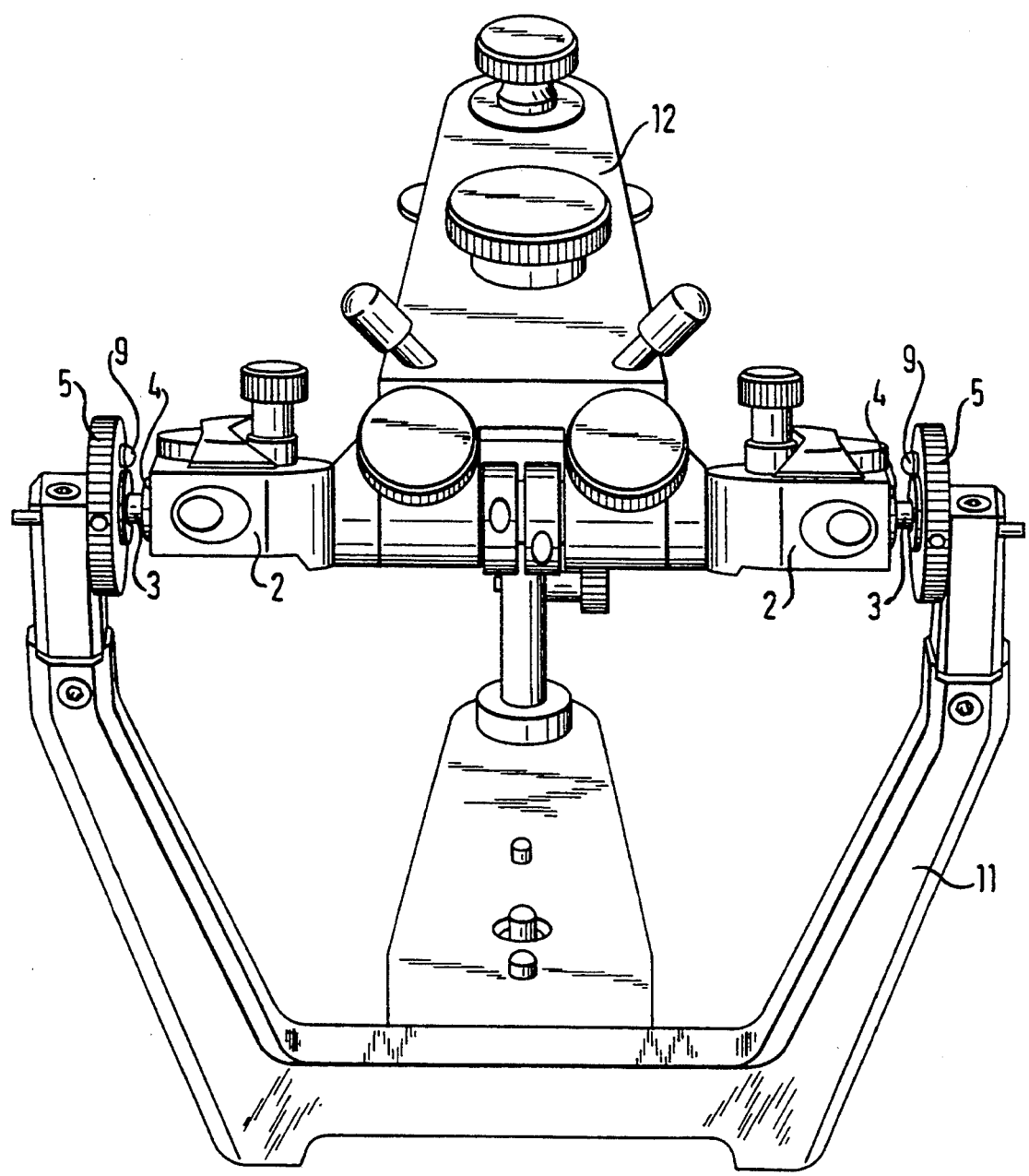
FIG. 1 shows a front view of the articulator of the invention.

In the figures the reference numerals have the following meanings:
1 ball
2 ball socket
3 ball neck
4 semi-circular ledge
5 ring
6 circular groove
7 circular recess in ball neck
8 spring-loaded ball
8a set screw
9 adjustable bolt
10 set screw for the bolt 9
11 lower part of the articulator
12 upper part thereof.

DESCRIPTION OF THE PREFERRED EMBODIMENT

FIG. 1 is an overall view of the articulator showing the ball housing 2 with the semi-circular ledge 4 thereon. The ring 5 is located in the unlocked state. The lower part of the articulator is referenced 11 and the upper part of the articulator is referenced 12. On the lower part 11 of the articulator the ball neck 3 is arranged horizontally to the left and to the right, such ball neck bearing the ball 1. The ball housings 2 are borne on the two balls.

Figure 2:
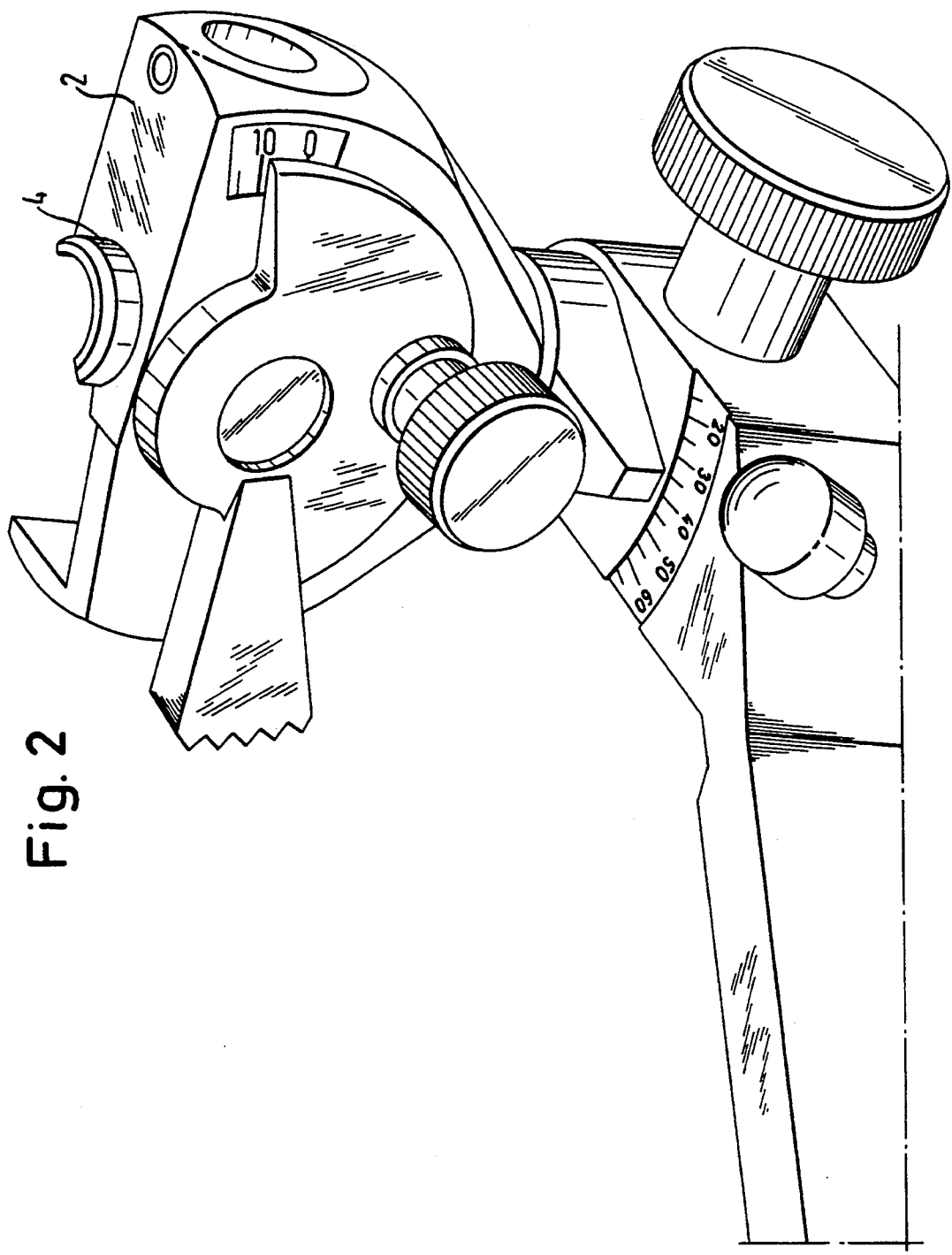
FIG. 2 shows a detailed view of the ball socket.

FIG. 2 shows in a more detailed view the ball housing 2 with the semi-circular ledge 4.

Figure 3:
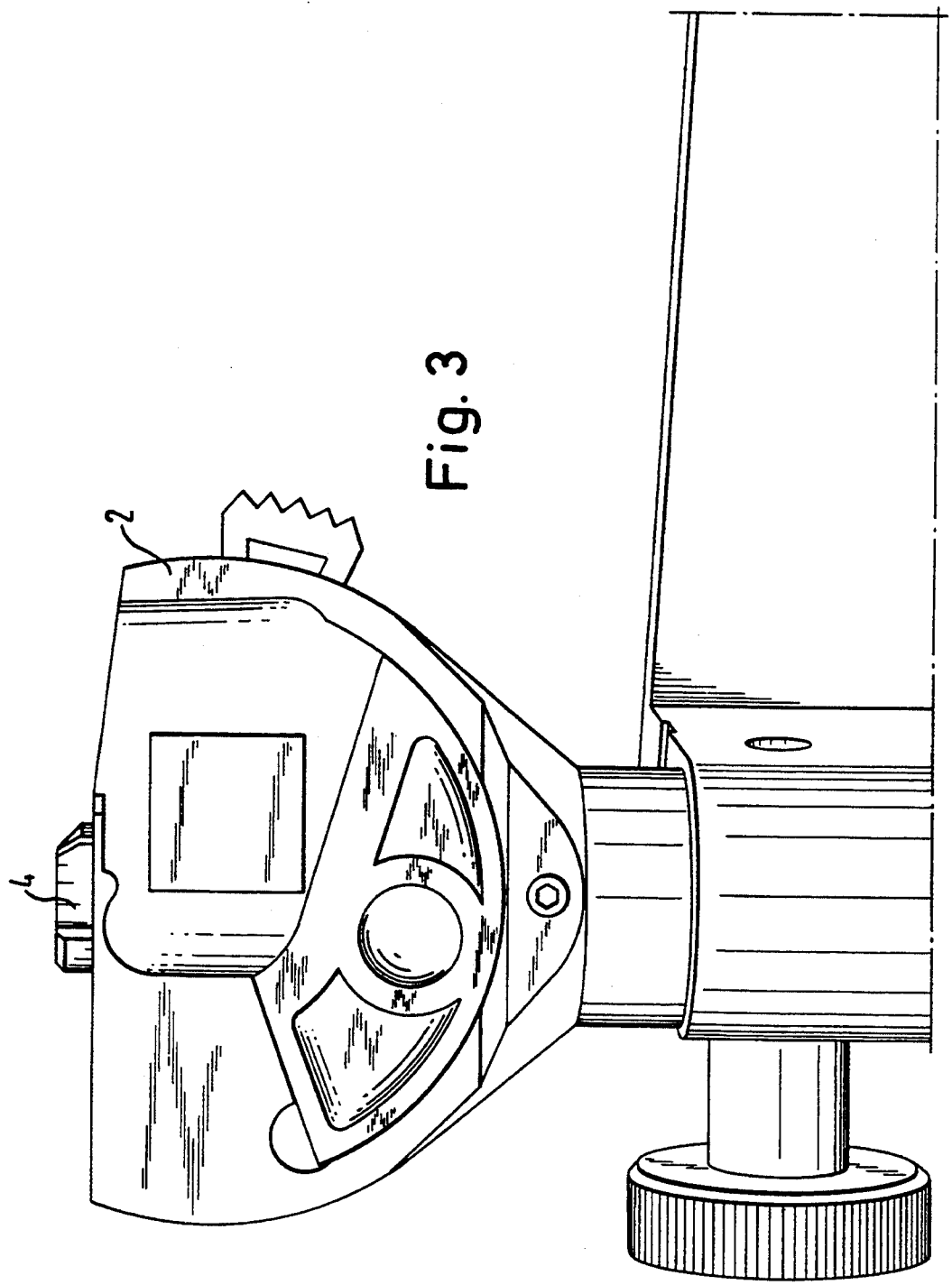
FIG. 3 shows the inner side of the semi-annular ledge located on the ball socket.

FIG. 3 shows, from a different angle, the inner side of the semi-circular ledge 4 located on the ball housing 2.

Figure 4:
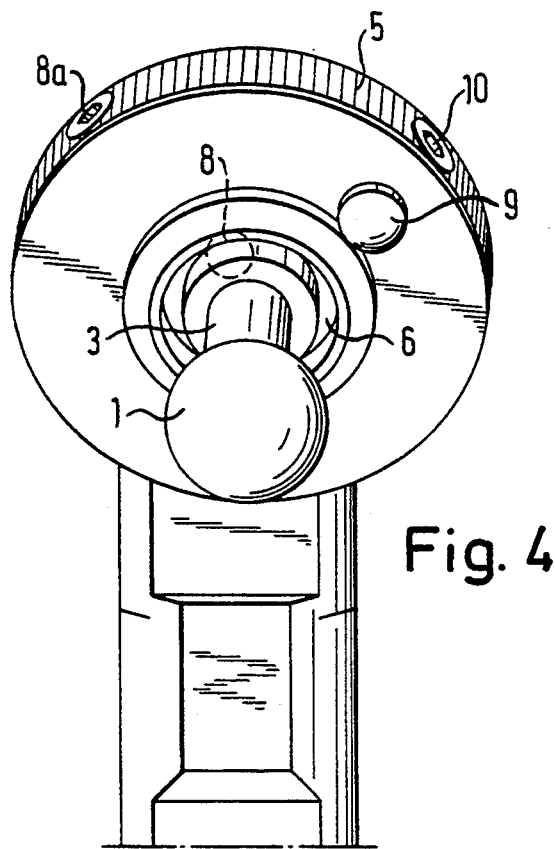
FIG. 4 shows a side view of the arrangement of the ball neck and the ball.

FIG. 4 shows the horizontally arranged ball neck 3 with the ball 1. A ring 5 having a circular groove 6 is arranged slidingly on the ball neck. The bolt 9 is adjustable using the locking screw 10.

Figure 5:
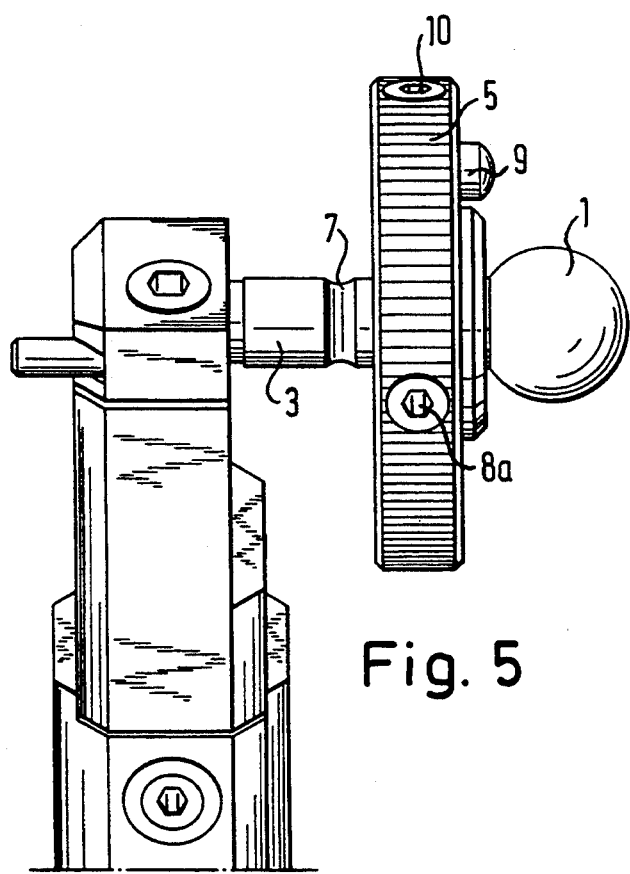
FIG. 5 shows a front view of the arrangement of the ball neck and the ball.

FIG. 5 shows in a horizontal arrangement the ball neck 3 with the ball 1 and the circular recess in the ball neck into which the one ball 8 fits, which is arranged in the ring 5 and is spring loaded. The spring loading force may be adjusted using the set screw 8a. The ring 5 includes screw threads corresponding to the set screw 8a. The bolt 9 is held in the desired setting by means of the screw 10.

Figure 6:
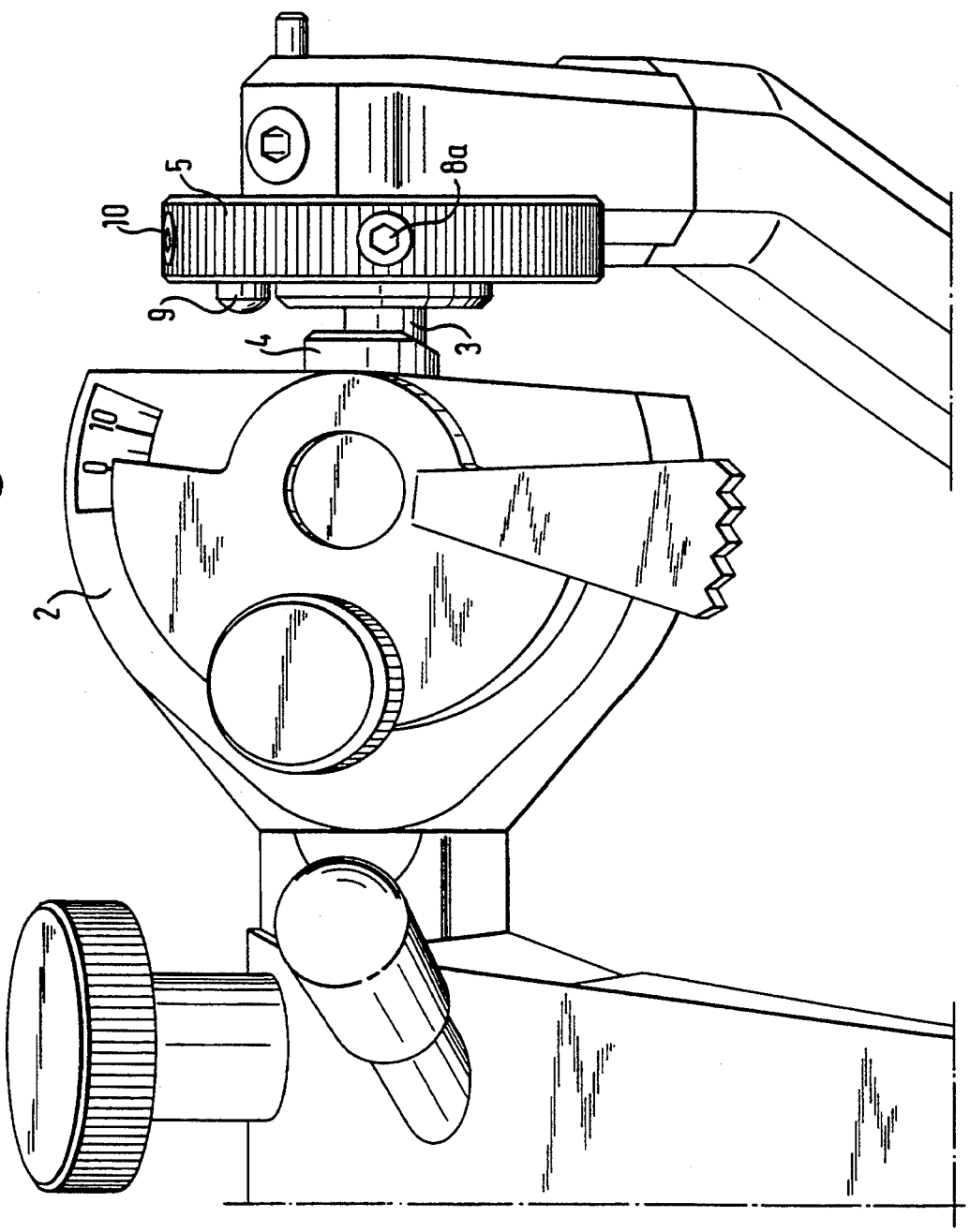
FIG. 6 shows the ball socket rested on the ball when the disk is in the unlocked position.

FIG. 6 indicates how the ball housing is rested on the ball 1, not illustrated. The semi-circular ledge 4 will clearly be seen arranged on the ball housing 2 and which fits into the circular groove in the ring 5. FIG. 6 shows the unlocked position.

Figure 7:
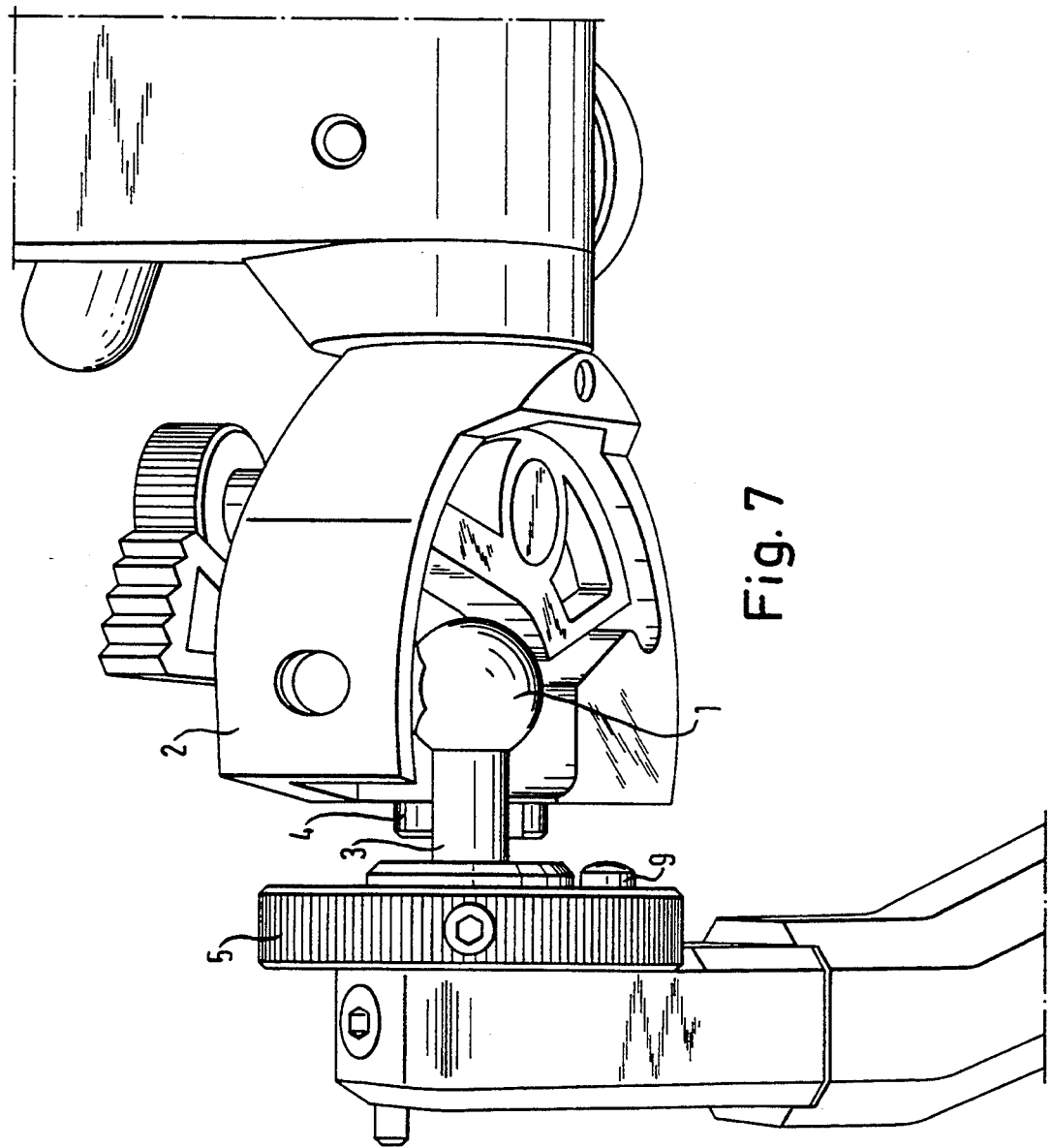
FIG. 7 shows the ball socket rested on the ball when the disk is in the locked position.

FIG. 7 shows the articulator from a different angle indicating how the ball housing 2 rests on the ball 1. Furthermore it is possible to clearly see how the semi-circular ledge 4 comes into engagement with the ball neck. In this case as well the ring 5 is in a locked condition. By moving the ring 5 to the right the semi-circular ledge 4 is caused to fit into the circular groove 6 in the ring 5.

Figure 8:
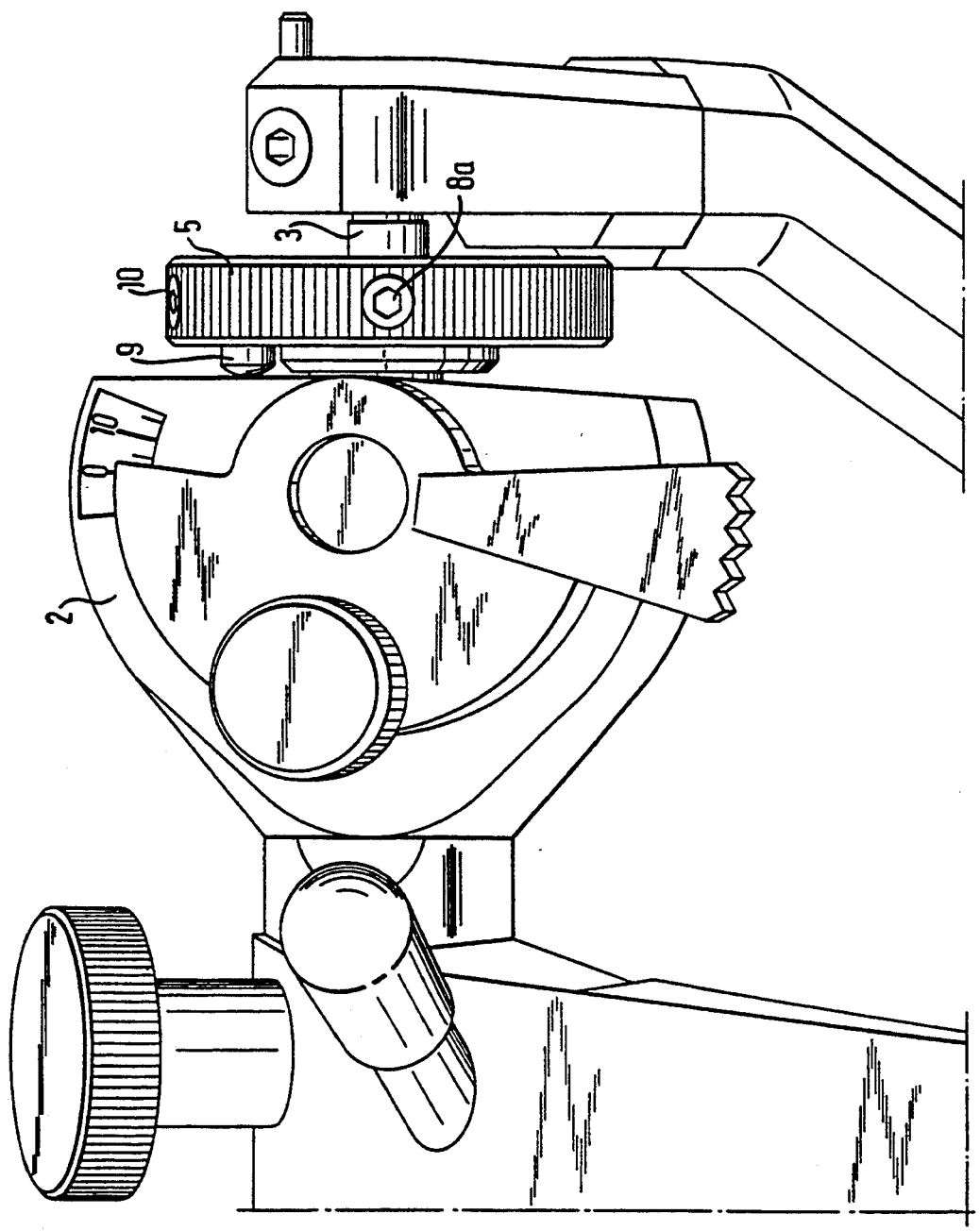
FIG. 8 shows the semi-annular ledge fitted into the annular groove in the disk in the locked condition.

FIG. 8 shows the locked condition of the semi-circular ledge 4 fitting into the circular groove 6 in the ring 5. Furthermore in this illustrated position the bolt 9 abuts against the ball housing 2. Accordingly the desired free transverse play is limited or completely taken up if the ring 5 is turned so that the bolt 9 does contact the ball housing 2. In this locked form a secure hinged connection between the ball and the ball housing is ensured so that satisfactory rotation or, respectively, a hinge function of the upper part of the articulator is guaranteed.

I claim:

1. A locking device for use in combination with an articulator, said articulator comprising a horizontally aligned ball neck, a ball on an end thereof and a ball housing being rested on the ball, said locking device providing a secure hinged connection between the ball and the ball housing, said locking device comprising:
   an axially movable and lockable ring arranged on the ball neck;
   a circular groove arranged on the ring on a side of the ring facing the ball; and
   a semi-circular ledge arranged on a side of the ball housing facing the ring, said ledge resiliently fitting into said circular groove when said locking device is in a locked condition.

2. The locking device according to claim 1 further comprising:
   a spring-loaded ball arranged in the ring;
   a circular groove extending perpendicular to a longitudinal axis of the ball neck, said spring-loaded ball being received into said groove; and
   a set screw for holding said spring-loaded ball in place and locking said ring axially.

3. The locking device according to claim 2 wherein the ring further comprises screw threads corresponding to the set screw.

4. The locking device according claim 1 further comprising an adjustable bolt on the side of the ring facing the ball for limiting a predetermined amount of free transverse play.

* * * * *